(12) United States Patent
Odani

(10) Patent No.: US 7,342,122 B2
(45) Date of Patent: Mar. 11, 2008

(54) BISPHOSPHONATE COMPLEXES

(75) Inventor: Akira Odani, Research Center for Materials Science, Nagoya University, Furo-cho, Chikusa-ku, Nagoya 464-8602 (JP)

(73) Assignee: Akira Odani, Nagoya (JP)

( * ) Notice: Subject to any disclaimer, the term of this patent is extended or adjusted under 35 U.S.C. 154(b) by 11 days.

(21) Appl. No.: 11/318,727

(22) Filed: Dec. 27, 2005

(65) Prior Publication Data

US 2006/0173185 A1    Aug. 3, 2006

Related U.S. Application Data

(63) Continuation of application No. PCT/IB2004/002722, filed on Jun. 28, 2004.

(60) Provisional application No. 60/483,218, filed on Jun. 27, 2003.

(51) Int. Cl.
*C07F 15/00* (2006.01)
*A61K 31/28* (2006.01)

(52) U.S. Cl. ............................ 556/17; 556/18; 556/24; 556/26; 546/2; 514/492

(58) Field of Classification Search .................. 556/17, 556/18, 24, 26; 546/2; 514/492
See application file for complete search history.

(56) References Cited

U.S. PATENT DOCUMENTS

| 4,291,027 | A | 9/1981 | Hoeschel et al. | 424/197 |
| 4,584,316 | A | 4/1986 | Rosenberg et al. | 514/492 |
| 5,602,115 | A | 2/1997 | Nugent | 514/105 |
| 5,728,650 | A | 3/1998 | Fisher et al. | 504/195 |
| 5,990,098 | A | 11/1999 | Van Beek et al. | 514/114 |
| 6,018,679 | A | 1/2000 | Dinh et al. | 604/20 |
| 6,087,349 | A | 7/2000 | Biller et al. | 514/108 |
| 6,114,316 | A | 9/2000 | Ramamurthy et al. | 514/108 |
| 6,214,812 | B1 | 4/2001 | Karpeisky et al. | 514/89 |
| 6,416,737 | B1 | 7/2002 | Manolagas et al. | 424/9.2 |
| 6,432,931 | B1 | 8/2002 | Reszka et al. | 514/108 |
| 6,436,386 | B1 | 8/2002 | Roberts et al. | 424/78.17 |
| 6,436,913 | B1 | 8/2002 | Asp | 514/102 |
| 6,455,514 | B2 | 9/2002 | Du Mesnil et al. | 514/108 |
| 6,517,867 | B2 | 2/2003 | Bechard et al. | 424/464 |
| 6,534,488 | B1 | 3/2003 | Gibson et al. | 514/102 |
| 6,559,139 | B1 | 5/2003 | Johnson et al. | 514/168 |
| 6,572,874 | B1 | 6/2003 | Pauletti et al. | 424/430 |

FOREIGN PATENT DOCUMENTS

| EP | 0 409 527 | 1/1991 |
| WO | WO 88/06149 | 8/1988 |
| WO | WO 03/051373 | 6/2003 |

OTHER PUBLICATIONS

Bose, R. et al., "Kinetics and mechanisms of platinum(II)-promoted hydrolysis of inorganic polyphosphates," Inorg. Chem., 1985, 24:3989-3996.
Galanski, M et al., "Synthesis, characterization, and in vitro antitumor activity of osteotropic siam(m)ineplantinum(II) complexes bearing a N,N-bis(phosphonomethyl)glycine ligand," J. Med. Chem., 2003, 46:4946-4951.
Goto, M. et al., "Intramolecular stacking of two aromatic rings in the platinum(II) coordination sphere: preparation, crystal structures, and 1H NMR spectra of bipyridine(N-arylmethyl-1,2-ethanediamine)platinum(II) nitrate," Bull. Chem. Soc. Jpn., 2000, 73:97-105.
Slavin, L. et al., "Phosphonato complexes of platinum(II): kinetics of formation and phosphorous-31 NMR characterization studies," J. Inorg. Biochem., 1990, 40:339-347.

*Primary Examiner*—Porfirio Nazario-Gonzalez
(74) *Attorney, Agent, or Firm*—Fish & Richardson; Alan F. Feeney; Pamela C. Ball

(57) ABSTRACT

Bisphosphonate compounds are disclosed, particularly bisphosonate conjugates useful in the treatment of soft tissues surrounding bone and bone-related diseases, such as bone cancer and osteoporosis.

23 Claims, 6 Drawing Sheets

Conditions : [Pt] 0.95mM at 35C° in 100mM HEPES buffer (pD=7.8)
Conditions of carboplatin : [Pt] 0.95mM at 35C° in 2mM HEPES buffer (pD=7.8)
measurements by $^{31}$PNMR and $^1$HNMR; (*) denotes measurements by AAS.

BISPHOSPHONATE COMPLEXES

CROSS-REFERENCE TO RELATED APPLICATIONS

This application is a continuation of copending international (PCT) application No. PCT/IB2004/002722, filed Jun. 28, 2004, designating the United States, which application claims priority to U.S. provisional application 60/483,218 filed Jun. 27, 2003.

FIELD OF THE INVENTION

The present invention is directed to particular bisphosphonate compounds, and in particular, to bisphosphonate conjugates that are useful in the treatment of soft tissues surrounding bone and bone-related diseases, such as bone cancer and osteoporosis.

BACKGROUND OF THE INVENTION

Bisphosphonates represent a class of drugs that have shown very promising therapeutic efficacy in the treatment of a number of diseases associated with abnormally accelerated bone resorption including; osteoporosis, Paget's disease and hypercalcemia of malignancy. Fleisch H., Ann Med, 29, 55-62 (1997) and Fleisch H., Drugs, 42, 919-944 (1991). More recently bisphosphonates have been shown to be effective at lowering the risk of developing skeletal complications (e.g., pathologic fractures, spinal-cord compression, the need for bone surgery or irradiation) in patients with prostate cancer that had spread to the bone, Saad F et al., J National Cancer Institute 94:1458-1468, 2002; and to inhibit the proliferation of RAS-dependent malignancies, e.g., small cell lung cancer Matsumoto, et al., Am. Soc. of Clin. Oncology, 2003, Abst. No. 2750. Bisphosphonates have also been shown to have antiangiogenic activty, Wood et al, J Pharmacol Exp Ther 2002 September; 302(3):1055-61. Bisphosphonates are commonly used for treatment of myeloma bone disease and against osteolytic metastases of breast cancer, and clinical studies have suggested their use to relieve pain in metastatic prostate cancer.

Platinum-based agents are widely utilized in chemotherapeutic applications. For example, cisplatin kills tumor cells via formation of covalent, cross- or intrastrand DNA adducts (Sherman et al. Chem. Rev., 87, 1153-81 (1987); Chu, J. Biol. Chem., 269, 787-90 (1994)). Treatment with such platinum-based agents thereby leads to the inhibition of DNA synthesis (Howle et al., Biochem. Pharmacol., 19, 2757-62 (1970); Salles et al., Biochem. Biophys. Res. Commun., 112, 555-63 (1983)). Thus, cells actively synthesizing DNA are highly sensitive to cisplatin (Roberts et al., Prog. Nucl. Acid Res. Mol. Biol., 22, 71-133 (1979); Pinto et al., Proc. Nat. Acad. Sci. (Wash.) 82, 4616-19 (1985)). Such cells generally experience a growth arrest in $G_2$ and eventually undergo apoptosis. This apoptotic effect is observed at drug concentrations insufficient to inhibit DNA synthesis (Sorenson et al, J. Natl. Cancer Inst., 82, 749-55 (1990)), suggesting that platinum agents act on neoplastic cells via multiple mechanisms. Some cells also demonstrate increased platinum sensitivity when in the $G_1$ phase of the cell cycle (Krishnaswamy et al., Mutation Res., 293, 161-72 (1993); Donaldson et al., Int. J. Cancer, 57, 847-55 (1994)). Upon release from $G_0/G_1$-S block, such cells remain maximally sensitized through the remainder of the cell cycle.

U.S. Pat. No. 6,087,349 discloses that bisphosphonates can act as protein-prenyl transferase inhibitors.

U.S. Pat. No. 4,746,654 discloses bisphosphonates useful as anti-inflammatory agents.

Australian Patent A-5 1534/85 discloses bisphosphonates useful in treating abnormal calcium and phosphorous metabolism and useful in treating arthritis.

U.S. Pat. No. 3,683,080 discloses polyphosphonates, in particular diphosphonates useful in inhibiting anomalous deposition and mobilization of calcium phosphate in animal tissue.

DE 3,719,513-A (Derwent 89-000580/01) discloses diphosphonic acid derivatives useful in treatment of disorders of calcium metabolism.

WO88/06158 discloses the reaction of activated methylenes with vinylidene diphosphonates.

International Publication Number WO90/12017 for International Application Number PCT/US90/01106 discloses geminal bisphosphonic acids and derivatives thereof as anti-arthritic agents.

United States Patent Application No. 20020022603 discloses compositions of zwitterionic phospholipids and bisphosphonates and use of such compositions as bisphosphate delivery systems with reduced GI toxicity.

United States Patent Application No. 20030032628 discloses pharmaceutical compositions of bisphosphonic acids, and salts thereof, prepared by wet granulation tablet formulation. These pharmaceutical compositions are said to be prepared without the addition of binder; instead, the drug itself acts as a binder.

United States Patent Application 20020002140 discloses glycosides and orthoester glyco side derivatives of bisphosphonate compounds which are said to have markedly enhanced intestinal absorption and enhanced bioavailability.

U.S. Pat. No. 5,133,972 discloses transdermal delivery phosphate compounds, and in particular bisphosphonates. Relatedly, U.S. Pat. No. 6,018,679 discloses a method for iontophoretically removing compounds capable of causing skin irritation or other harmful effects.

U.S. Pat. No. 6,114,316 discloses compositions which combine a tetracycline and a bisphosphonate in synergistic proteinase inhibiting amounts to treat or prevent tissue-destructive conditions related to excess proteinase activity in a biological system.

U.S. Pat. No. 6,214,812 discloses bisphosphonate conjugates which are said to be capable of releasing antibacterial and/or cytotoxic components upon binding with bone tissue.

U.S. Pat. No. 6,436,386 discloses hydroxyapatite-targeting polymeric structures, and biologically active conjugates thereof, wherein the hydroxyapatite-targeting moiety may be a bisphosphonate. The conjugates are said to provide a means for tethering a biologically active substances to bone surface.

Numerous other references may be found in the art describing various types of bisphosphonate compounds, conjugates, formulations, combinations and uses thereof. However there is not disclosed therein a method of synthesizing bisphosphonate complexes comprising platinum, palladium, or like moieties, that are therapeutically useful. Other bisphosphonate complexes known in the art were not known to possess superior properties in respect of their use as therapeutic agents, particularly in respect of their use for the treatment of cancer, more particularly with respect to their use for the treatment of cancers affecting bone tissue.

SUMMARY OF THE INVENTION

The present invention relates to bisphosphonate complexes and their use as targeted cytostatic and/or cytotoxic agents. Desirably the bisphosphonate complexes of the invention may be used to target cells, e.g., cancerous cells, associated with bone.

In a first aspect the invention relates to a complex according to formula I:

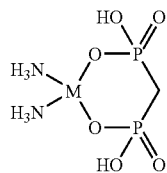
(I)

wherein M is Pt(II) or Pd(II);

or a pharmaceutically acceptable salt thereof.

In a preferred embodiment of said first aspect M is Pt(II).

In a second aspect, the invention relates to a complex according to formula II:

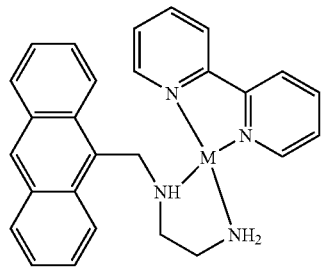
(II)

wherein M is Pt(II) or Pd(II);

or a pharmaceutically acceptable salt thereof.

In a preferred embodiment of said second aspect M is Pt(II).

In a third aspect, the invention relates to a complex according to formula III:

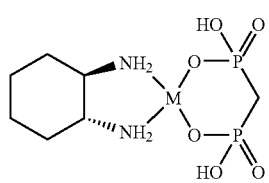
(III)

wherein M is Pt(II) or Pd(II);

or a pharmaceutically acceptable salt thereof.

In a preferred embodiment of said third aspect M is Pt(II).

In a fourth aspect, the invention relates to a complex according to formula IV:

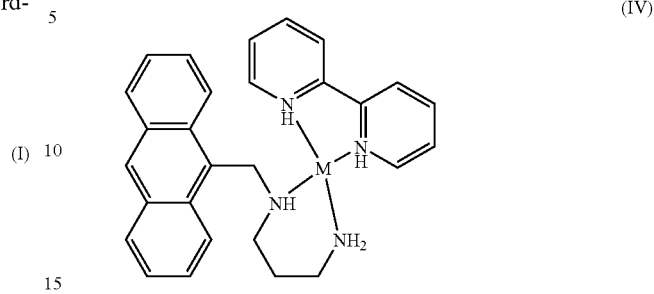
(IV)

wherein M is Pt(II) or Pd(II);

or a pharmaceutically acceptable salt thereof.

In a preferred embodiment of said fourth aspect M is Pt(II).

In a fifth aspect, the invention relates to a complex according to formula V:

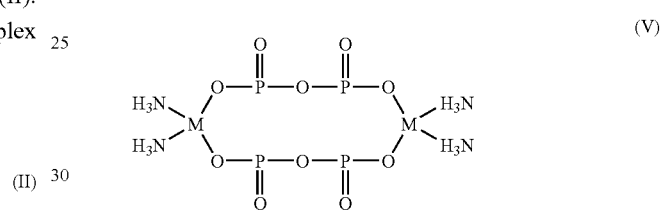
(V)

wherein M is Pt(II) or Pd(II);

or a pharmaceutically acceptable salt thereof.

In a preferred embodiment of said fifth aspect M is Pt(II).

In a sixth aspect, the invention relates to a complex according to formula VI:

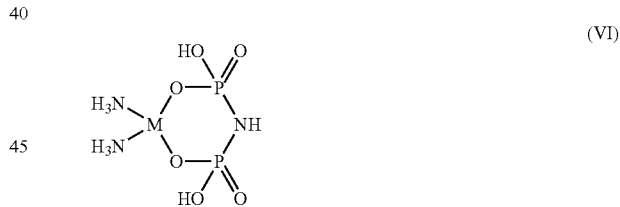
(VI)

wherein M is Pt(II) or Pd(II);

or a pharmaceutically acceptable salt thereof.

In a preferred embodiment of said sixth aspect M is Pt(II).

In a seventh aspect, the invention relates to a complex according to formula VII:

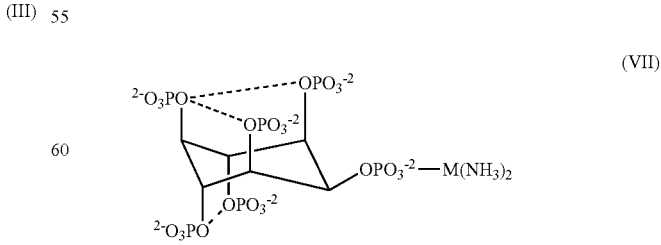
(VII)

wherein M is Pt(II) or Pd(II);

or a pharmaceutically acceptable salt thereof.

In a preferred embodiment of said seventh aspect M is Pt(II).

In a eighth aspect, the invention relates to a complex according to formula VIII:

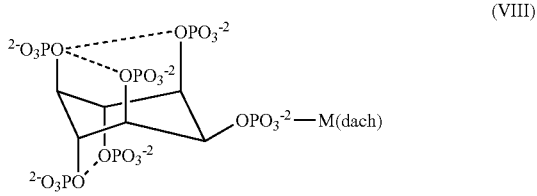
(VIII)

wherein M is Pt(II) or Pd(II);

or a pharmaceutically acceptable salt thereof.

In a preferred embodiment of said eighth aspect M is Pt(II).

In a ninth aspect, the invention relates to a process for synthesizing a compound according to formula I comprising performing the synthetic procedure described for examples of formula I substantially as herein described. In a preferred embodiment of said ninth aspect M is Pt(II).

In a tenth aspect, the invention relates to a process for synthesizing a compound according to formula II comprising performing the synthetic procedure described for examples of formula II substantially as herein described. In a preferred embodiment of said tenth aspect M is Pt(II).

In eleventh aspect, the invention relates to a process for synthesizing a compound according to formula III comprising performing the synthetic procedure described for examples of formula III substantially as herein described. In a preferred embodiment of said aspect M is Pt(II).

In a twelfth aspect, the invention relates to a method of delivering a cytostaticly and/or cytotoxicly effective amount of platinum or palladium, or of a platinum-containing or a palladium-containing moiety, to a subject in need thereof, said method comprising administering a therapeutically effective amount of a compound according to formula I, or a pharmaceutically acceptable salt thereof, to said subject in need thereof. Preferably M in formula I is platinum. Also preferably said method comprises delivering said compound at or to bone tissue within said subject. More preferably said method comprises delivering said compound at or to bone tissue on which or in which cancer cells are present. More preferably still said therapeutically effective amount of said compound is an amount effective to treat, i.e., to inhibit and/or to kill, said cancer cells.

In an thirteenth aspect, the invention relates to a method of delivering a cytostaticly and/or cytotoxicly effective amount of platinum or palladium, or of a platinum-containing or a palladium-containing moiety, to a subject in need thereof, said method comprising administering a therapeutically effective amount of a compound according to formula II, or a pharmaceutically acceptable salt thereof, to said subject in need thereof. Preferably M in formula II is platinum. Also preferably said method comprises delivering said compound at or to bone tissue within said subject. More preferably said method comprises delivering said compound at or to bone tissue on which or in which cancer cells are present. More preferably still said therapeutically effective amount of said compound is an amount effective to treat, i.e., to inhibit and/or to kill, said cancer cells.

In a fourteenth aspect, the invention relates to a method of delivering a cytostaticly and/or cytotoxicly effective amount of platinum or palladium, or of a platinum-containing or a palladium-containing moiety, to a subject in need thereof, said method comprising administering a therapeutically effective amount of a compound according to formula III, or a pharmaceutically acceptable salt thereof, to said subject in need thereof. Preferably M in formula III is platinum. Also preferably said method comprises delivering said compound at or to bone tissue within said subject. More preferably said method comprises delivering said compound at or to bone tissue on which or in which cancer cells are present. More preferably still said therapeutically effective amount of said compound is an amount effective to treat, i.e., to inhibit and/or to kill, said cancer cells.

DETAILED DESCRIPTION OF THE PREFERRED EMBODIMENT

Figure 1:
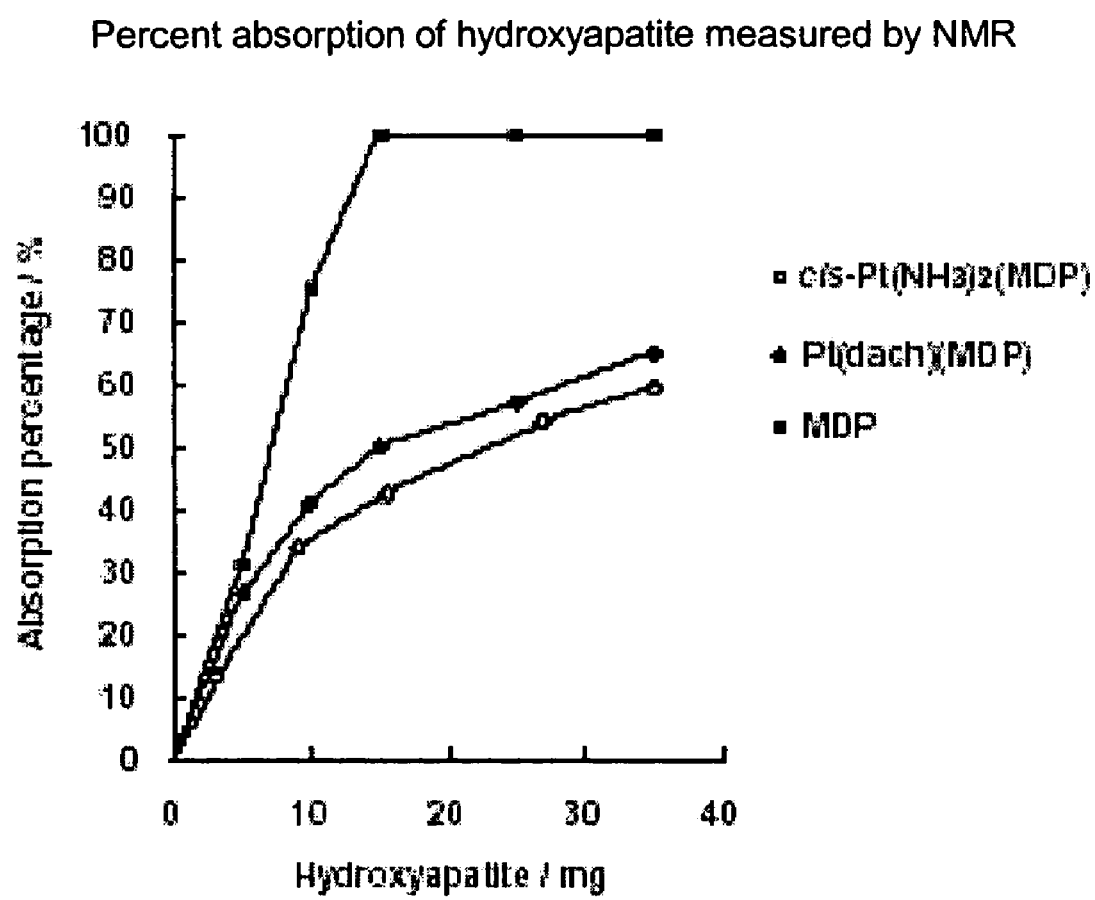
FIG. 1 is a graph showing the adsorption percentages of the test compounds to hydroxyapatite as measured by NMR.

The following experimental results are provided for purposes of illustration and are not intended to limit the scope of the invention.

EXAMPLE 1 cis-Pt(NH$_3$)$_2$(MDP)

a. Materials

Bisphosphonate (methylenediphosphinic acid (MDP)) was purchased from Tokyo-Kasei, K$_2$PtCl$_4$ was from Tanaka, dimethylacetamide (DMA) and other reagents were Nakarai Tesque. All chemicals were of highest grade available and used without further purification. Water was deionized, doubly distilled, and finally purified by a Milli-Q.

b. Procedure

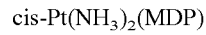

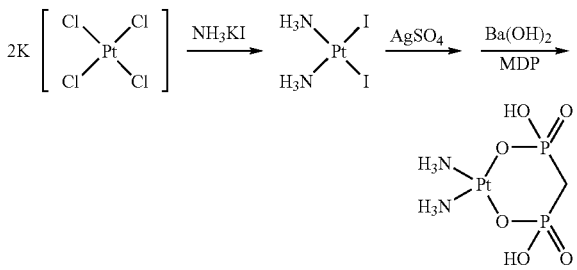

b.1. cis-Pt(NH$_3$)$_2$I$_2$

According the literature (S. C. Dhara, Indian J. Chem, 1970, 8.), KI 3.3 g (19.8 mmol) was added to K$_2$PtCl$_4$ 2 g (4.8 mmol) in 20 ml H$_2$O. The solution was stirred in water bath for 5 min and then added to 47 mL of 0.21M aqueous NH$_3$ solution. After standing at room temperature for about 3 hr the deposited yellow powder was filtered off and washed with hot water, EtOH, and ether. Yield 91%. Elemental analysis: calculated: H, 1.25%, N, 5.80%; observed: H, 1.08%, N, 5.58%. IR: 3260 cm$^{-1}$, 3200 cm$^{-1}$, 1282 cm$^{-1}$, 1270 cm$^{-1}$.

b.2. cis-Pt(NH$_3$)$_2$(MDP)

0.20 g (0.5 mmol) of cis-Pt(NH$_3$)$_2$I$_2$ from step b.1. in dimethylacetamide 5 ml was added to a suspension of 0.149 g (0.48 mmol) of Ag$_2$SO$_4$ in 20 mL H$_2$O and stirred for about 4 hr in the dark. After filtration by membrane filter Ba(OH)$_2$.8H$_2$O 0.15 g (0.48 mmol) and MDP 0.12 g (0.70 mmol) in 20 mL H$_2$O was added. After stirring overnight the solution was concentrated by evaporation and the resulting powder was reprecipitated using H$_2$O-EtOH. Yield 35%

Elemental analysis:

| calculated: | C: 2.98% H: 2.50%, N: 6.95% |
| observed: | C: 3.14% H: 2.50%, N: 6.83% |

NNMR: $^{31}$P NMR (D$_2$O, 85% H$_3$PO$_4$) d (ppm)+27.25; $^1$H NMR (D$_2$O) d(ppm) 2.349 (t, J=19.91 Hz);

EXAMPLE 2

Pt(dach)(MDP)

a. Materials 1R,2R-1,2-cyclohexanediamine (dach) was purchased from Tokyo-Kasei; K$_2$PtCl$_4$ was purchased from Tanaka; dimethylacetamide (DMA) and other reagents were purchased from Nakarai Tesque. All chemicals were of the highest grade available and were used without further purification. Water was deionized, distilled, and finally purified by Milli-Q.

b. Procedure

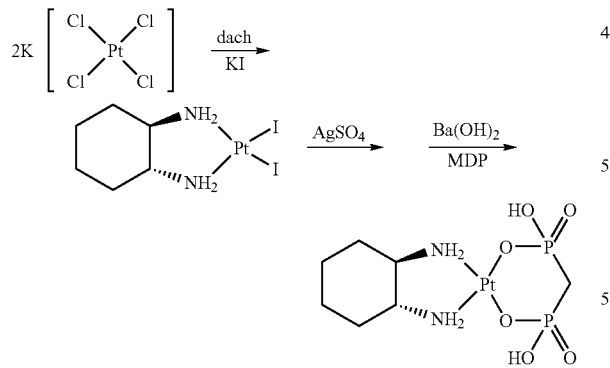

b.1. Pt(dach)I$_2$

KI 2.0 g (12 mmol) was added to K$_2$PtCl$_4$ 1.25 g (3 mmol) in 20 ml H$_2$O. The solution was stirred in a water bath (50° C.) for about 5 min. and then added to 1R,2R-1,2-cyclohexanediamine 0.34 g (3 mmol). The reaction mixture was stirred overnight at room temperature and the deposited yellow powder was filtered off and washed with hot water, then EtOH, and finally diethyl ether. Yield 90%.

Elemental analysis:

| calculated: | C: 12.80%, H: 2.51%, N: 4.98%; |
| observed: | C: 12.66%, H: 2.27%, N: 5.01%. | b.2. Pt(dach)(MDP)

0.28 g (0.5 mmol) of Pt(dach)I$_2$ from step b.1. in dimethylacetamide 5 ml was added to a suspension of 0.149 g (0.48 mmol) of Ag$_2$SO$_4$ in 20 mL H$_2$O and stirred for about 4 hr. in the dark. After filtration by membrane filter Ba(OH)$_2$.8H$_2$O 0.156 g (0.48 mmol) and MDP 0.129 g (0.75 mmol) in 20 mL H$_2$O was added. After stirring for about 2 hr., 1 ml of 0.5M H$_2$SO$_4$ aqueous solution was added to the reaction solution mixture over about 5 min. with stirring. The mixture was filtrated and concentrated to about 5 ml by evaporation and the white powder was re-precipitated using MeOH. Yield 35%.

Elemental analysis:

| calculated: | C: 17.40%, H: 3.75%, N: 5.80%; |
| observed: | C: 17.47%, H: 3.44%, N: 5.89%. |

NNMR: $^{31}$P NMR (D$_2$O, 85% H$_3$PO$_4$)_(ppm) +26.1; $^1$H NMR (D$_2$O)_(ppm) 1.16(t, 2H, dach CH), 1.29(m, 4H, dach), 1.56(d, 2H, dach), 202(d, 2H, dach), 2.37(t, MDP, J=19.91 Hz); $^{195}$Pt NMR (D$_2$O, [Pt(en)$_2$]Cl$_2$)_(ppm) –4378

EXAMPLE 3

N-(9-Anthranyl)methyl-1,2-ethanediamine Dihydrochloride (Aten•2HCl)

a. Materials

N-(9-Anthranyl)aldehyde was purchased from Tokyo-Kasei; K$_2$PtCl$_4$ was purchased from Tanaka; PdCl$_2$ was purchased from Kishida Chemical; 2,2'-bipyridine (bpy) was purchased from Wako; DMSO and other reagents were from Nakarai Tesque. All chemicals were of highest grade available and used without further purification. Water was deionized, doubly distilled, and finally purified by a Milli-Q.

b. Procedure

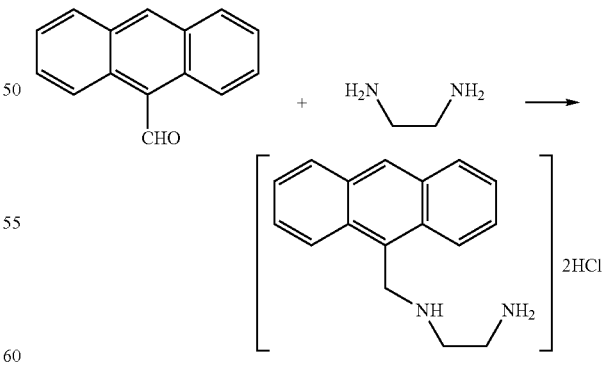

Ethylendiamine 6.00 g (100 mmol) was added to N-(9-Anthranyl)aldehyde 2.06 g (10 mmol) in 200 ml 1:1 dioxane-CHCl$_3$ and the solution was refluxed for about 3 hr. After cooling to room temperature, the solution was concentrated by evaporation and 0.45 g (12 mmol) of NaBH$_4$ in MeOH was added. After stirring overnight 6N HCl was added to adjust the pH to 1 and the liquid was evaporated. Aqueous NaOH was added and the basic solution was extracted with CHCl$_3$ and dried using Na$_2$SO$_4$. The CHCl$_3$ phase was evaporated and the oil residue was treated with MeOH/6N HCl. The resulting yellowish powder was recovered by filtration and recrystallized from EtOH—H$_2$O. Yield 2.2 g (65%)

Elemental analysis C$_{17}$H$_{20}$N$_2$Cl$_2$.0.75H$_2$O

| | |
|---|---|
| calculated: | C: 60.63%, H: 6.43%, N: 8.32% |
| observed: | C: 60.40%, H: 6.45%, N: 7.81% |

$^1$H NMR (D$_2$O, 300 MHz) d=3.42 (t, 2H), 3.67 (t, 2H), 5.27 (s, 2H), 7.64 (t, 2H), 7.75 (t, 2H), 8.16 (d, 2H), 8.26 (d, 2H), 8.65 (s, 1H)

EXAMPLE 4

Pt(bpy)(Aten) Complex a. Pt(bpy)Cl$_2$ 1.411 g (3.4 mmol) of K$_2$PtCl$_4$ in a solution of 10 mL H$_2$O, 30 mL DMSO was added to 0.531 g (3.4 mmol) of bpy 50 mL DMSO and the mixture was heated to 80° C. for about 3 hr with stirring. The reaction was stirred overnight and the resulting yellow needles were filtered off and washed with H$_2$O and ether. Yield 1.2 g (81%)

Elemental analysis: C$_{10}$H$_8$N$_2$Cl$_2$Pt

| | |
|---|---|
| calculated: | C: 28.45%, H: 1.91%, N: 6.58% |
| observed: | C: 28.65%, H: 1.95%, N: 6.64% | b. [Pt(bpy)(Aten)]Cl$_2$

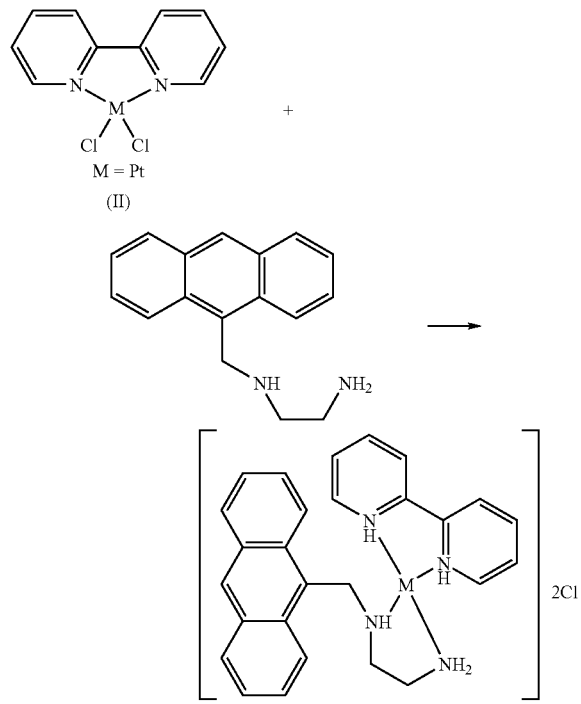

According the literature (Goto, M., et al., Bull. Chem. Soc. Jpn. 2000, 73, 97-105.), to a suspension of Pt(bpy)Cl$_2$ (0.429, 1.0 mmol) in 20 ml of H$_2$O were added 0.44 g (1.3 mmol) Aten•2HCl.0.75H$_2$O and 0.16 g (1.5 mmol) Na$_2$CO$_3$ and the mixture was stirred at 80° C. for about 2.5 h. The mixture was then filtered while still hot to remove small amounts of undissolved materials. After cooling to room temperature a pale-yellow precipitate formed which was collected on a filter and dried in a desiccator. Yield 0.56 g (79%)

Elemental analysis: C$_{27}$H$_{26}$N$_4$ Cl$_2$ Pt.2H$_2$O

| | |
|---|---|
| calculated: | C: 45.77%, H: 4.27%, N: 7.91% |
| observed: | C: 45.51%, H: 4.05%, N: 7.61% |

EXAMPLE 5

Pd(bpy)(Aten) Complex a. Pd(bpy)Cl$_2$

PdCl$_2$ 0.89 g (5.0 mmol) and NaCl 0.58 g (10.0 mmol) were suspended in 50 mL H$_2$O and stirred for about 1 hr. After filtration the solution was added to a solution of 0.78 g (5.0 mmol) bpy in 20 mL MeOH and the resulting solution stirred overnight. A yellowish powder precipitated which was recovered and washed with H$_2$O and EtOH. Yield 1.56 g (93%)

Elemental analysis: C$_{10}$H$_8$N$_2$Cl$_2$Pd

| | |
|---|---|
| calculated: | C: 36.01%, H: 2.42%, N: 8.40% |
| observed: | C: 35.94%, H: 2.14%, N: 8.31% | b. Pd(bpy)(Aten)]Cl$_2$

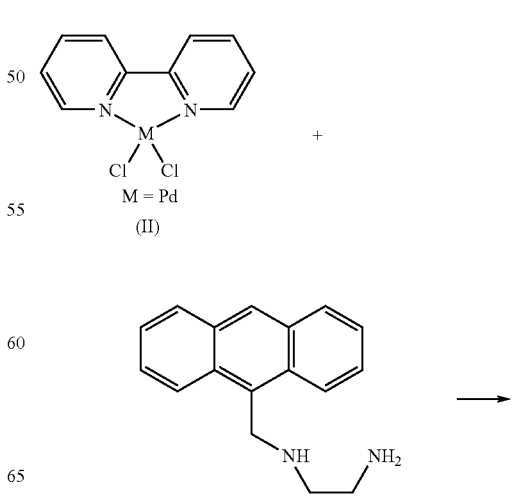

-continued

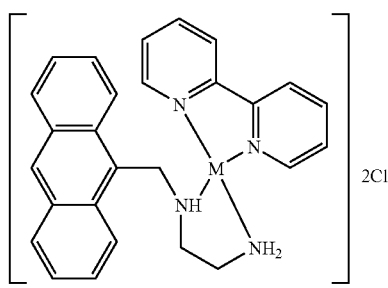

0.33 g (1.0 mmol) of Pd(bpy)Cl₂ from the immediately foregoing step were suspended in 10 mL H₂O. 0.44 g (1.3 mmol) of Aten•2HCl.0.75H₂O and 0.16 g (1.5 mmol) Na₂CO₃ were added and the mixture was then heated to 80° C. for about 2 hr. The solution was filtered while still hot then concentrated by evaporation. A yellow powder was deposited on standing at room temperature. Yield 0.43 g (68%)

Elemental analysis $C_{27}H_{26}N_4Cl_2Pd.3H_2O$

| calculated: | C: 50.84%, H: 5.06%, N: 8.78% |
| observed: | C: 50.89%, H: 4.69%, N: 8.80% |

EXAMPLE 6

Pd(bpy)(AtC₃)

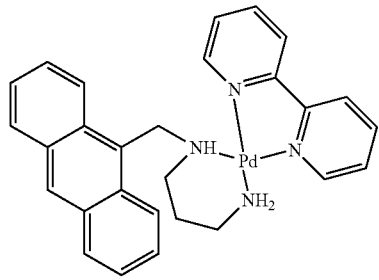

a. AtC₃•2HCl 1,3-diaminepropane 7.41 g (100 mmol) was added to N-(9-Anthranyl)aldehyde 2.06 g (10 mmol) in 200 ml 1:1 dioxane-CHCl₃ and the solution was refluxed for about 3 hr. After cooling to room temperature, the solution was concentrated by evaporation and 0.45 g (12 mmol) of NaBH₄ in MeOH was added. After stirring overnight 6N HCl was added to adjust the pH to 1 and the solution was evaporated. Aqueous NaOH was added and the basic solution was extracted with CHCl₃ and dried by using Na₂SO₄. The CHCl₃ phase was evaporated and the oil residue was treated with MeOH/6N HCl. The resulting yellowish powder was recovered by filtration and recrystallized from EtOH—H₂O. Yield 70%

Elemental analysis: $C_{18}H_{22}N_2Cl_2$

| Calculated: | C 64.10% H 6.57% N 8.31% |
| Observed: | C 64.40% H 6.38% N 7.98% |

NMR: ¹H NMR (CDCl₃, TMS) d (ppm) 1.64(2H,m), 2.72(2H, t), 2.88(2H, t), 4.66(2H, s), 7.39(4H, m), 7.94(2H, d), 8.25(2H, t), 8.33(1H, s)

b. [Pd(bpy)(AtC3)]Cl₂

0.33 g (1.0 mmol) of Pd(bpy)Cl₂ from the immediately foregoing step were suspended in 10 ml H₂O. 0.44 g (1.3 mmol) of AtC₃.2HCl and 0.16 g (1.5 mmol) Na₂CO₃ were added and the mixture was then heated to 80° C. for about 2 hr. The solution was filtered while still hot then concentrated by evaporation. A yellow powder was deposited on standing at room temperature. Yield 0.40 g (58%)

Elemental analysis: $C_{28}H_{28}N_4Pd_1Cl_2.H_2O$

| Calculated: | C 54.60% | H 4.91% | N 9.10% |
| Observed: | C 54.40% | H 4.48% | N 8.98% |

EXAMPLE 7

Pt(bpy)(AtC₃)

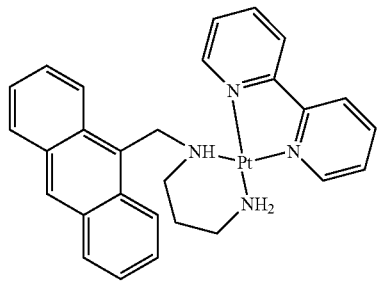

Synthesis of [Pt(bpy)(AtC3)]Cl₂

According the literature (Goto, M., et al., Bull. Chem. Soc. Jpn. 2000, 73, 97-105.), to a suspension of Pt(bpy)Cl₂ (0.42 g, 1.0 mmol) in 20 ml of H₂O were added 0.44 g (1.3 mmol) AtC₃.2HCl and 0.16 g (1.5 mmol) Na₂CO₃ and the mixture was stirred at 80° C. for about 3 h. The mixture was then filtered while still hot to remove small amounts of undissolved materials. After cooling to room temperature a pale-yellow precipitate formed which was collected on a filter and dried in a desiccator. Yield 0.60 g (73%)

Elemental analysis: C, 28; H, 28; N, 4; Pt, 1; Cl, 2;

| calculated: | C: 48.99% | H 4.11%, | N: 8.16% |
| observed: | C: 49.13% | H 4.37% | N: 8.08% |
| | 48.78 | 4.29 | 8.01 |

1H NMR (D2O, DSS)d(ppm) 8.91(1H, d), 8.53(1H,d), 8.35(3H,m), 8.05(2H,t), 7.75(6H,m), 7.18(2H, m), 6.91(1H, d), 6.36(1H, t), 5.55(1H, d), 3.50(4H, m), 3.01(1H, t), 2.51(2H, m)

EXAMPLE 8 cis-Pt (NH$_3$)$_2$(Pyrophosphate)

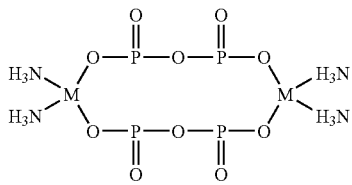

Synthesis of cis-Pt(NH$_3$)$_2$(Pyrophosphate)

0.482 g (1 mmol) of cis-Pt(NH$_3$)$_2$I$_2$. in dimethylacetamide 5 ml was added to a suspension of 0.306 g (0.98 mmol) of Ag$_2$SO$_4$ in 40 mL H$_2$O and stirred for about 4 hr in the dark. After filtration by membrane filter Ba(OH)$_2$.8H$_2$O 0.305 g (1.00 mmol) in 80 mL H$_2$O was added and stirred for 30 min. After filtration, pH of the solution was adjusted 3-4 by NaOH aqueous solution and 1:1 pyrophosphoric acid (2.0 mmol):H$_2$O 0.5 g was added and stirred for 1 hr. After filtration the solution was concentrated by evaporation and the resulting powder was precipitated by adding MeOH. The greenish powder was dissolved in hot water. The filtered solution was concentrated in vacuo and MeOH was added. The white powder deposited was washed with ether. Yield 30%

Elemental analysis: H$_8$N$_2$O$_6$P$_2$Pt.1H$_2$O

| calculated: | H: 1.91%, | N: 6.65% |
| observed: | H: 2.28, 2.27% | N: 6.90, 6.62% |

$^{31}$P NMR (D$_2$O, 85% H$_3$PO$_4$): δ(ppm) 0 ppm

EXAMPLE 9

Pt(NH$_3$)—IP6  Pt(NH$_3$)$_2$.IP6.10Na.7H$_2$O

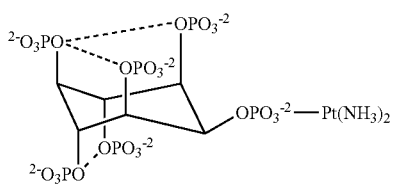

Synthesis of cis-Pt(NH$_3$)$_2$.IP6 cis-Pt(NH$_3$)$_2$I$_2$ 0.483 g (1.0 mmol) dissolved in N,N-dimethylacetamide 5 ml was added to a suspension of AgNO$_3$ 0.340 g (2.0 mmol) in H$_2$O 40 ml, and stirred for a overnight in the dark. After filtration by membrane filter, IP6•12Na 1.013 g (1.0 mmol) in H$_2$O 30 ml was added and stirred for 3 hrs. The solution was concentrated by evaporation and the resulting powder was reprecipitated by adding MeOH. Yield 54%.

Elemental analysis: C, 6; H, 26; N, 2; O, 31; P, 6; Pt, 1; Na, 10;

| calculated: | C 5.84% | H 2.11% | N 2.27% |
| observed: | C 5.95% | H 2.15% | N 2.12% |

$^{31}$P NMR (D$_2$O, 85% H$_3$PO$_4$) δ (ppm) +7.87(1P), +5.24 (2P), +4.92(2P), +3.98(1P) $^{195}$Pt NMR (D$_2$O, Pt(en)$_2$Cl$_2$)δ (ppm)–2819 XRF Calculated: P, 6.00; Na, 10.0; Pt, 1.00. Observed: P, 6.00; Na, 10.9; Pt, 0.94.

EXAMPLE 10

Pt(dach)-IP6

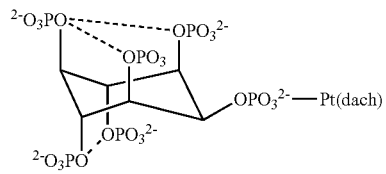

Synthesis of cis-Pt(dach)•IP6 cis-Pt(dach)I$_2$ 0.563 g (1.0 mmol) dissolved in N,N-dimethylacetamide 5 ml was added to a suspension of AgNO$_3$ 0.340 g (2.0 mmol) in H$_2$O 20 ml, and stirred for a overnight in the dark. After filtration by membrane filter, IP6•12Na 1.013 g (1.0 mmol) in H$_2$O 30 ml was added and stirred for 3 hrs. The solution was concentrated by evaporation and the resulting powder was reprecipitated by adding MeOH 100 ml. Yield 73%.

Elemental analysis: C$_{12}$H$_{44}$N$_2$O$_{36}$P$_6$Pt$_1$Na$_{10}$

| calculated: | C 10.26% | H 3.14% | N 2.00% |
| observed: | C 10.13% | H 2.88% | N 1.71% |

XRF Calculated: P, 6.00; Na, 10.0; Pt, 1.00. Observed: P, 6.00; Na, 10.3; Pt, 1.42. $^{31}$P NMR (D$_2$O, 85% H$_3$PO$_4$)δ (ppm) +7.60(1P), +5.26(2P), +5.00(2P), +4.03(2P) $^{195}$Pt NMR (D$_2$O, Pt(en)$_2$Cl$_2$)δ(ppm) –3209

EXAMPLE 11

Pt(NH$_3$)$_2$(NDP)

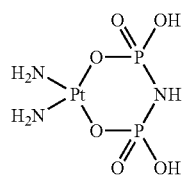

Synthesis of cis-Pt(NH$_3$)$_2$.NDP 0.20 g (0.5 mmol) of cis-Pt(NH$_3$)$_2$I$_2$ from step b.1. in dimethylacetamide 5 ml was added to a suspension of 0.149 g (0.48 mmol) of Ag$_2$SO$_4$ in 20 mL H$_2$O and stirred for about 4 hr in the dark. After filtration by membrane filter Ba (OH)$_2$.8H$_2$O 0.15 g (0.48 mmol) and sodium iminodiphosphate (NDP) 0.19 g (0.70 mmol) in 20 ml H$_2$O was added. After stirring overnight 1M HClO$_4$ aqueous solution 1.4 ml was added and the solution was concentrated by evaporation and the resulting powder was reprecipitated using H$_2$O-EtOH. Yield 35%

Elemental Analysis: H$_9$N$_3$O$_6$P$_2$Pt$_1$.1H$_2$O

| calculated: | H 2.24% | N 10.40% |
| observed: | H 1.99% | N 10.01% |

$^{31}$P NMR (D$_2$O, 85% H$_3$PO$_4$)d(ppm) +10

EXAMPLE 12

Pt(NH$_3$)$_2$(MDPOH)

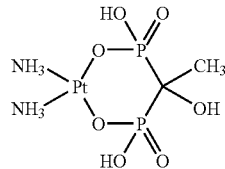

Synthesis of cis-Pt(NH$_3$)$_2$.MDPOH 0.20 g (0.5 mmol) of cis-Pt(NH$_3$)$_2$I$_2$. in dimethylacetamide 5 ml was added to a suspension of 0.149 g (0.48 mmol) of Ag$_2$SO$_4$ in 20 ml H$_2$O and stirred for about 4 hr in the dark. After filtration by membrane filter Ba(OH)$_2$.8H$_2$O 0.15 g (0.48 mmol) and 60% 1-hydroxyethane-1,1-bis(phosphonic acid) (etidronic acid, MDPOH) 0.24 g (0.70 mmol) in 20 ml H$_2$O was added. After stirring overnight the solution was concentrated by evaporation and the resulting powder was reprecipitated using H$_2$O-EtOH. Yield 65%

Elemental analysis: C$_2$H$_{12}$N$_2$O$_7$P$_2$Pt$_1$

| calculated: | C: 5.54% | H: 2.50% | N: 6.95% |
| observed: | C: 5.46% | H: 2.30% | N: 6.76% |

EXAMPLE 13

In Vitro Assay—Cell Growth Inhibition a. Materials & Method

KB cells were purchased from Human Science Research Resource Bank (Osaka, Japan). The cells were cultured in Earle's MEM (GIBCO BRL) containing 10% FBS (Bio Whittaker) at 37° C. under 5% CO$_2$. After 24 hours the test compounds were added to the cells at the indicated concentrations. 72 hours later the cells were stained with tripan blue and counted manually. IC$_{50}$ is calculated as the concentration (aqueous solution) of complex required to inhibit growth of cells by 50%. The results are given in Tables 1, 2 and 3.

b. Results

TABLE 1

|  | 5 µM | 15 µM | 50 µM | 150 µM | 500 µM |
|---|---|---|---|---|---|
| cis-Platinum | 28.20% | 13.80% | 6.78% | 4.34% | 3.52% |
|  | (±0.14) | ±1.83 | ±0.07 | ±0.3 | ±0.13 |
| cis-Pt(NH$_3$)$_2$(MDP) | 59.30% | 38.20% | 23.70% | 20.00% | 16.43% |
|  | ±2.96 | ±3.81 | ±0.67 | ±1.05 | ±3.17 |

TABLE 2

|  | 1 µg/ml | 3 µg/mL | 10 µg/mL | 30 µg/mL | 100 µg/mL |
|---|---|---|---|---|---|
| [Pt(bpy)(Aten)]Cl$_2$ | 93.8% (±1.7) | 81.4% (±2.7) | 75.3% (±5.9) | 73.2% (±9.1) | 32.5% (±1.2) |
| cis-Pt(NH$_3$)$_2$Cl$_2$ | 17.0% (±3.2) | 13.4% (±1.3) | 3.0% (±1.5) | 2.2% (±0.7) | 1.6% (±0.4) |
| [Pd(bpy)(Aten)]Cl$_2$ | 86.9 (±7.9) | 81.4 (±8.6) | 75.1 (±4.0) | 44.7 (±2.0) | 12.3 (±3.1) |
| ([Pd(bpy)(Npen)]Cl$_2$) | 85.6 (±8.6) | 81.3 (±11.0) | 74.6 (±9.8) | 61.4 (±10.7) | 2.4 (±0.3) |

TABLE 3

|  | IC$_{50}$ (µM) |
|---|---|
| cis-Pt(NH$_3$)$_2$Cl$_2$ | 2.75 |
| cis-Pt(NH$_3$)$_2$(MDP) | 7.50 |
| [Pt(bpy)(Aten)]Cl$_2$ | 97 µM |
| [Pd(bpy)(Aten)]Cl$_2$ | 36 µM |

In a similar fashion a representative number of examples of compounds of the invention were tested for their ability to inhibit the growth/proliferation of cell types representing a number of different cancers. The results are provided in Tables 4-13, below, which provide the Inhibition Constants (IC$_{50}$, µM) for each compound across various cell lines.

TABLE 4

Breast Cancer Cell Lines

| Ex. No. | HBC-4 | BSY-1 | HBC-5 | MCF-7 | MDA-MB-231 |
|---|---|---|---|---|---|
| 1 | −4.00 | −4.60 | −4.47 | −4.35 | −4.00 |
| 8 | −4.83 | −5.20 | −5.57 | −4.77 | −4.35 |
| 2 | −4.57 | −4.00 | −5.18 | −4.83 | −4.00 |
| 4 | −4.14 | −4.89 | −4.12 | −4.23 | −4.50 |
| 5 | −4.91 | −5.34 | −4.98 | −5.28 | −5.29 |
| 9 | −4.27 | −4.71 | −5.16 | −4.19 | −4.06 |
| 10 | −5.07 | −4.56 | −5.40 | −5.32 | −4.67 |
| 11 | −4.72 | −4.78 | −5.09 | −4.71 | −4.23 |
| 7 | −5.76 | −5.89 | −5.89 | −5.69 | −5.78 |
| 6 | −5.76 | −5.78 | −5.89 | −5.67 | −5.66 |
| 12 | −4.00 | −4.00 | −4.00 | −4.00 | −4.00 |

TABLE 5

Brain Cancer Cell Lines

| Ex. No. | U251 | SF-268 | SF-295 | SF-539 | SNB-75 | SNB-78 |
|---|---|---|---|---|---|---|
| 1 | −4.00 | −4.00 | −4.00 | −4.00 | −4.00 | −4.25 |
| 8 | −4.64 | −5.11 | −5.22 | −5.17 | −4.93 | −4.61 |
| 2 | −4.00 | −4.00 | −4.04 | −4.72 | −4.00 | −4.00 |
| 4 | −4.84 | −4.83 | −4.90 | −4.82 | −4.77 | −4.56 |
| 5 | −5.00 | −5.27 | −5.31 | −5.36 | −5.16 | −4.67 |
| 9 | −4.00 | −4.26 | −4.46 | −4.00 | −5.51 | −4.29 |
| 10 | −4.69 | −4.52 | −4.67 | −5.14 | −4.86 | −4.48 |
| 11 | −4.50 | −4.52 | −4.71 | −4.54 | −4.37 | −4.41 |
| 7 | −5.66 | −5.62 | −5.62 | −5.75 | −5.59 | −5.54 |
| 6 | −5.68 | −5.68 | −5.68 | −5.79 | −5.63 | −5.65 |
| 12 | −4.00 | −4.00 | −4.00 | −4.00 | −4.00 | −4.00 |

TABLE 6

Colon cancer Cell Lines

| Ex. No. | HCC2998 | KM-12 | HT-29 | HCT-15 | HCT-116 |
|---|---|---|---|---|---|
| 1 | −4.00 | −4.00 | −4.00 | −4.00 | −4.00 |
| 8 | −4.57 | −4.43 | −4.44 | −4.51 | −4.58 |
| 2 | −4.00 | −4.00 | −4.72 | −4.29 | −5.06 |
| 4 | −4.81 | −4.77 | −4.57 | −4.00 | −4.37 |
| 5 | −5.54 | −5.22 | −5.25 | −5.14 | −5.38 |
| 9 | −4.00 | −4.00 | −4.00 | −4.00 | −4.41 |
| 10 | −4.70 | −4.23 | −4.65 | −5.14 | −5.33 |
| 11 | −4.44 | −4.00 | −4.38 | −4.27 | −4.48 |
| 7 | −5.70 | −5.69 | −5.69 | −5.56 | −5.72 |
| 6 | −5.73 | −5.67 | −5.68 | −5.59 | −5.76 |
| 12 | −4.00 | −4.00 | −4.00 | −4.00 | −4.00 |

TABLE 7

Lung cancer Cell Lines

| Ex. No. | NCI-H23 | NCI-H226 | NCI-H522 | NCI-H460 | A549 | DMS273 | DMS114 |
|---|---|---|---|---|---|---|---|
| 1 | −4.00 | −4.00 | −4.64 | −4.00 | −4.00 | −4.00 | −4.00 |
| 8 | −5.20 | −4.64 | −5.16 | −5.22 | −4.79 | −4.97 | −4.85 |
| 2 | −4.17 | −5.21 | −5.18 | −4.65 | −4.63 | −5.00 | −4.15 |
| 4 | −4.18 | −4.83 | −4.00 | −5.23 | −4.69 | −4.85 | −4.89 |
| 5 | −4.88 | −5.41 | −5.22 | −5.86 | −4.88 | −5.24 | −5.28 |
| 9 | −4.70 | −4.00 | −5.69 | −4.46 | −4.00 | −4.29 | −4.72 |
| 10 | −4.95 | −5.08 | −5.17 | −5.19 | −5.21 | −6.27 | −4.26 |
| 11 | −4.68 | −4.51 | −4.80 | −4.90 | −4.61 | −4.60 | −4.55 |
| 7 | −5.53 | −5.64 | −5.77 | −5.71 | −5.68 | −5.68 | −5.76 |
| 6 | −5.53 | −5.54 | −5.72 | −5.70 | −5.69 | −5.68 | −5.74 |
| 12 | −4.00 | −4.00 | −4.00 | −4.00 | −4.00 | −4.00 | −4.00 |

TABLE 8

Melanoma Cell Line

| Ex. No. | LOX-IMVI |
|---|---|
| 1 | −4.00 |
| 8 | −4.85 |
| 2 | −4.59 |
| 4 | −4.46 |
| 5 | −5.15 |
| 9 | −4.08 |
| 10 | −5.31 |
| 11 | −4.66 |
| 7 | −5.76 |
| 6 | −5.73 |
| 12 | −4.00 |

TABLE 9

Ovarian cancer Cell Lines

| Ex. No. | OVCAR-3 | OVCAR-4 | OVCAR-5 | OVCAR-8 | SK-OV-3 |
|---|---|---|---|---|---|
| 1 | −4.25 | −4.21 | −4.00 | −4.00 | −4.00 |
| 8 | −4.69 | −4.83 | −4.52 | −4.72 | −4.65 |
| 2 | −4.00 | −4.00 | −4.51 | −4.00 | −4.00 |
| 4 | −4.13 | −4.19 | −4.79 | −4.37 | −4.77 |
| 5 | −4.95 | −5.06 | −5.30 | −5.13 | −5.10 |
| 9 | −4.82 | −4.42 | −4.00 | −4.00 | −5.20 |
| 10 | −4.90 | −5.01 | −4.78 | −4.57 | −4.28 |
| 11 | −4.52 | −4.63 | −4.53 | −4.42 | −4.43 |
| 7 | −5.68 | −5.70 | −5.80 | −5.52 | −5.61 |
| 6 | −5.67 | −5.76 | −5.65 | −5.56 | −5.63 |
| 12 | −4.00 | −4.00 | −4.00 | −4.00 | −4.00 |

TABLE 10

Renal cancer

| Ex. No. | RXF-631L | ACHN |
|---|---|---|
| 1 | −4.00 | −4.00 |
| 8 | −4.74 | −5.37 |
| 2 | −4.12 | −4.16 |
| 4 | −4.89 | −4.20 |
| 5 | −5.43 | −5.22 |
| 9 | −4.37 | −5.37 |
| 10 | −4.39 | −5.21 |
| 11 | −4.73 | −4.76 |
| 7 | −5.67 | −5.67 |
| 6 | −5.67 | −5.71 |
| 12 | −4.00 | −4.00 |

TABLE 11

Human stomach cancer

| Ex. No. | St-4 | MKN1 | MKN7 | MKN28 | MKN45 | MKN74 |
|---|---|---|---|---|---|---|
| 1 | −4.00 | −4.00 | −4.55 | −4.00 | −4.00 | −4.00 |
| 8 | −4.61 | −5.18 | −4.76 | −4.52 | −4.91 | −4.50 |
| 2 | −4.00 | −4.00 | −4.00 | −4.00 | −5.51 | −4.00 |
| 4 | −4.74 | −4.00 | −4.45 | −4.34 | −4.68 | −4.75 |
| 5 | −5.12 | −5.28 | −5.04 | −4.86 | −5.08 | −5.33 |
| 9 | −4.00 | −4.42 | −4.00 | −4.00 | −4.14 | −4.00 |
| 10 | −4.30 | −4.89 | −4.17 | −4.19 | −6.21 | −4.15 |
| 11 | −4.44 | −4.60 | −4.47 | −4.21 | −4.60 | −4.27 |
| 7 | −5.61 | −5.60 | −5.62 | −5.64 | −5.63 | −5.63 |
| 6 | −5.51 | −5.64 | −5.64 | −5.57 | −5.63 | −5.70 |
| 12 | −4.00 | −4.00 | −4.00 | −4.00 | −4.00 | −4.00 |

TABLE 12

Prostatic cancer

| Ex. No. | DU-145 | PC-3 |
|---|---|---|
| 1 | −4.00 | −4.00 |
| 8 | −5.29 | −4.45 |
| 2 | −4.19 | −4.00 |
| 4 | −4.33 | −4.22 |
| 5 | −5.10 | −4.90 |
| 9 | −4.66 | −4.04 |
| 10 | −5.03 | −4.46 |
| 11 | −4.82 | −4.63 |
| 7 | −5.73 | −5.59 |
| 6 | −5.63 | −5.70 |
| 12 | −4.00 | −4.00 |

TABLE 13

Mean $IC_{50}$ (all cell types):

| | |
|---|---|
| 1 | −4.09 |
| 8 | −4.83 |
| 2 | −4.35 |
| 4 | −4.54 |
| 5 | −5.18 |
| 9 | −4.38 |
| 10 | −4.86 |
| 11 | −4.55 |
| 7 | −5.68 |
| 6 | −5.67 |
| 12 | −4.00 |

The forgoing data demonstrate that compounds of the invention exhibit significant inhibition of cancerous cells.

EXAMPLE 14

In Vitro Assay—Adsorption of Pt Complexes to Hydroxyapatite, $Ca_{10}(PO_4)_6(OH)_2$ Each of a 5, 10, 15, 25, 35, and 100 mg sample of hydroxyapatite (Bio-Rad Macro-Prep Ceramic Hydroxyapatite, type I, 40 μm) was added to 2 ml of HEPES buffer at pD=7.8 and the resulting mixture was shaken for about 24 h at 37° C. Then, 100 μl of each complexes dissolved in HEPES buffer at pD=7.8 was added and the mixtures were shaken for 1.5 h at 37° C. All suspensions were filtered, and these solutions were measured by $^{31}P$ NMR (Varian VXR-300S) and Atomic Absorption Spectrometry (Hitachi Z-5710 AAS) of platinum or, for carboplatin, by $^1H$ NMR. Percentage adsorption to hydroxyapatite was calculated as follows.

From NMR: Binding percentage/%=$[(A-B)/A]\times 100$

From AAS: Binding percentage/%=$[(C-D)/C]\times 100$

Figure 2:
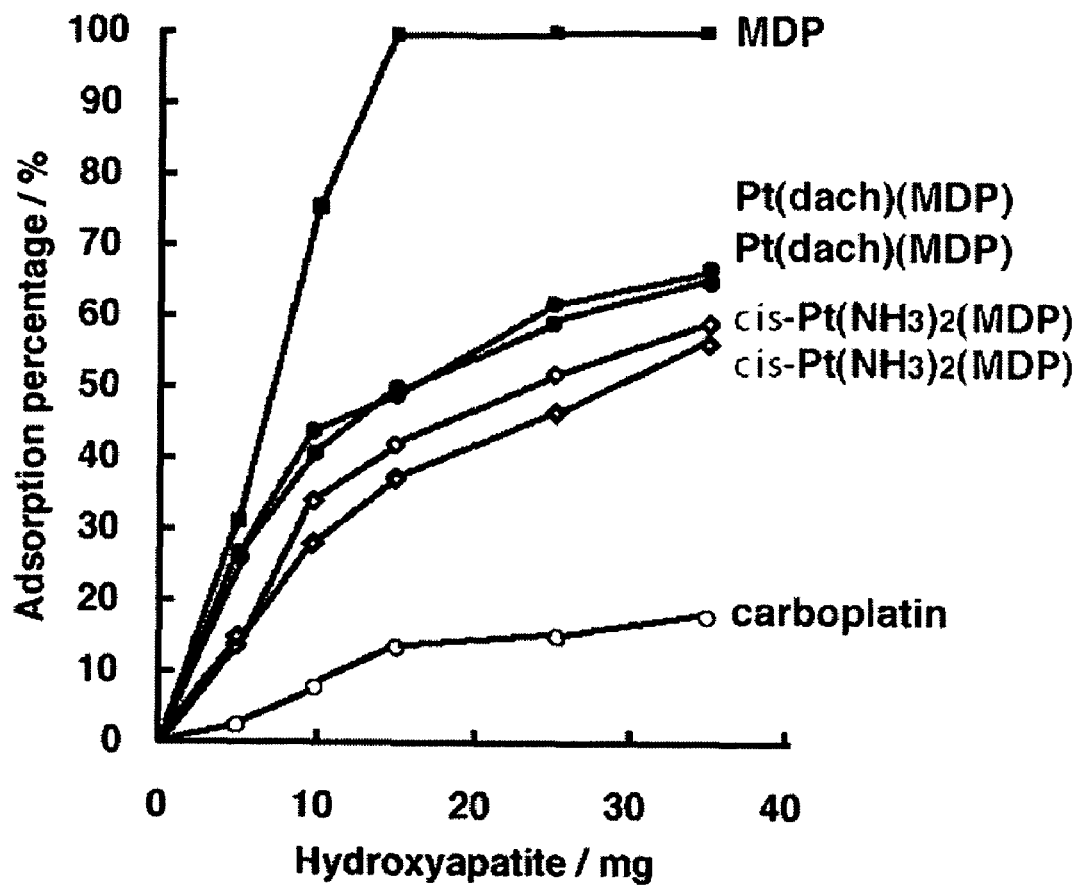
FIG. 2 is a graph showing the adsorption percentages of the test compounds to hydroxyapatite as measured by $^{31}P$ NMR, $^{1}H$ NMR, and AAS.
Figure 3:
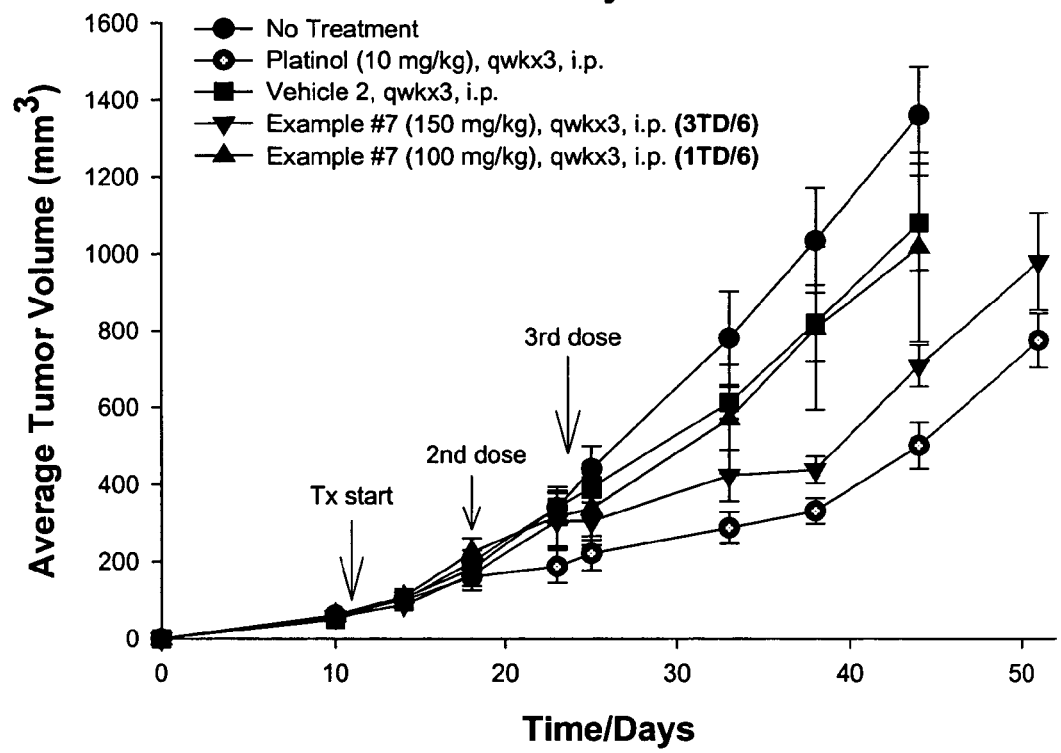
FIG. 3 is graph illustrating the effects of Example #7 against tumor model DU-145 in athymic nude mice.
Figure 4:
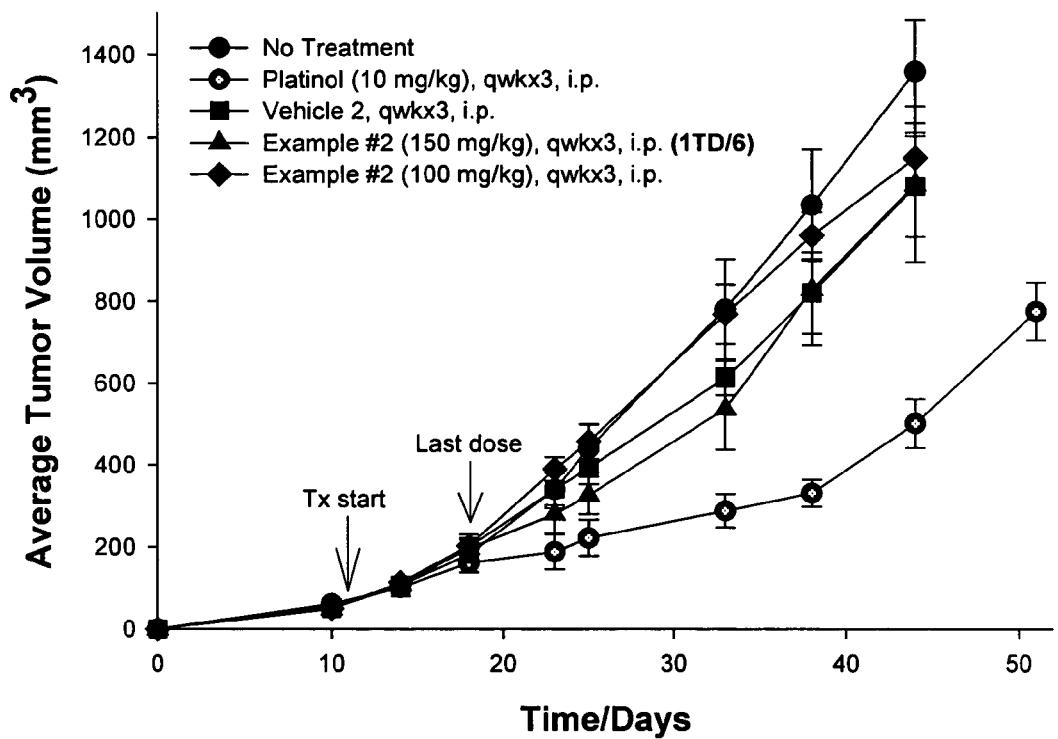
FIG. 4 is a graph illustrating the effects of Example #2 against tumor model DU-145 in athymic nude mice.
Figure 5:
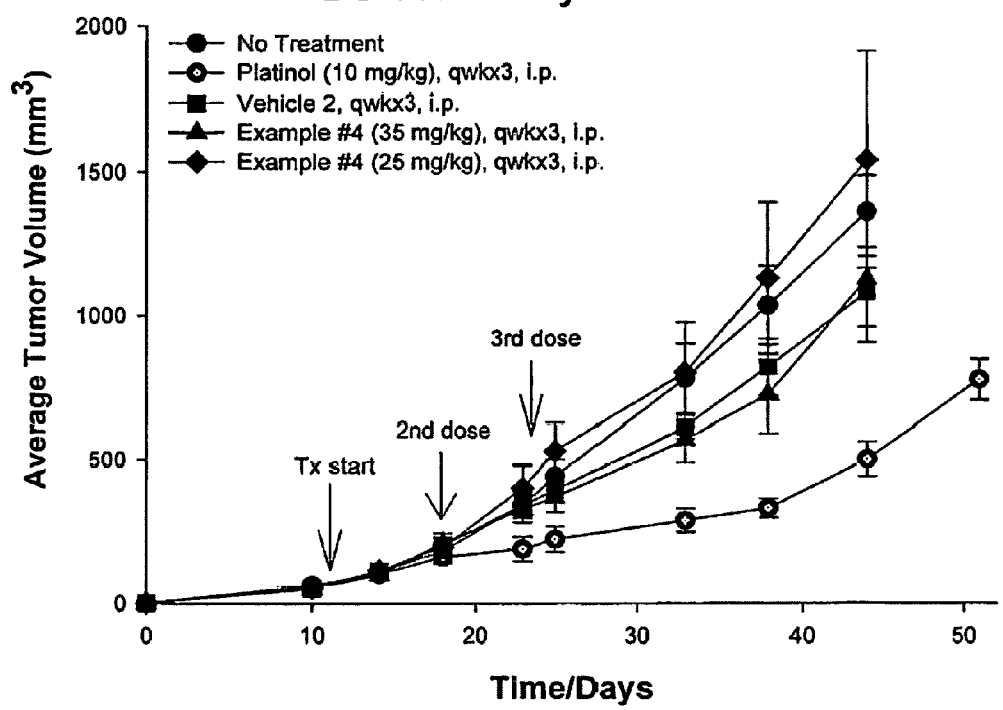
FIG. 5 is a graph illustrating the effects of Example #4 against tumor model DU-145 in athymic nude mice.
Figure 6:
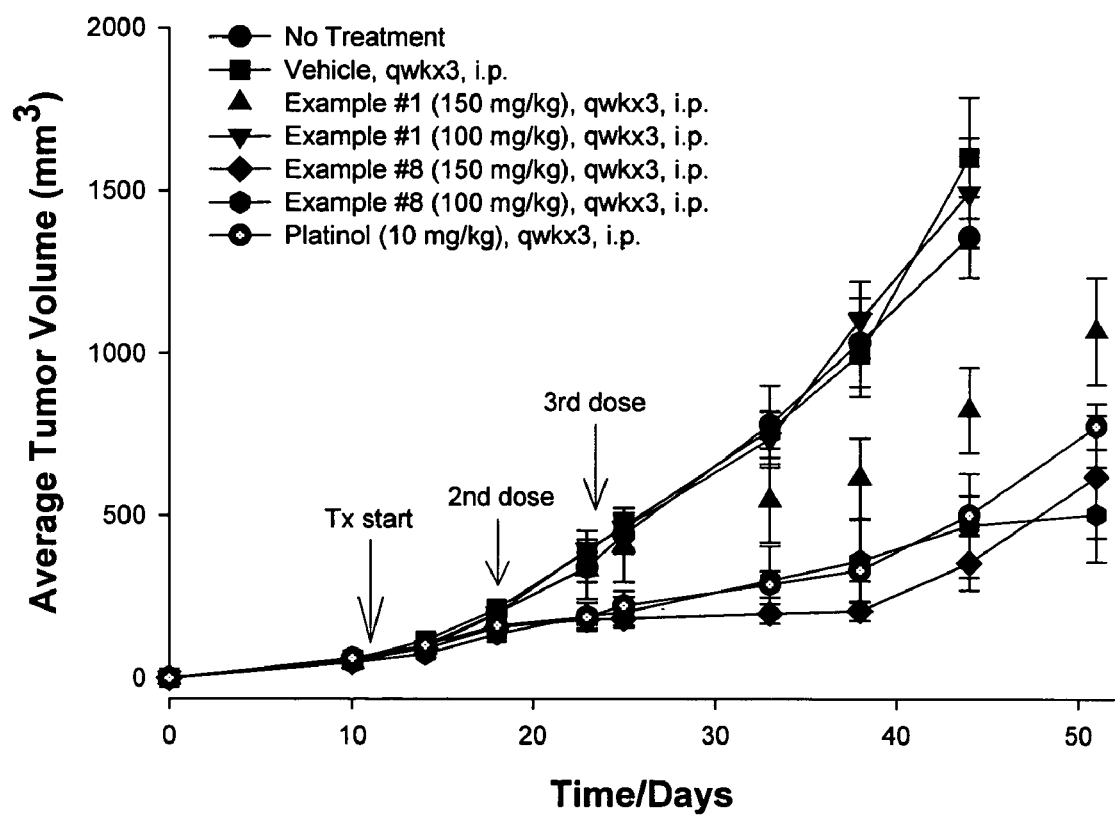
FIG. 6 is graph illustrating the effects of Examples #1 and #8 against tumor model DU-145 in athymic nude mice.

A=the integration intensity of Pt(II) complex
B=the integration intensity of Pt(II) complex after reacted with hydroxyapatite
C=the concentration of Pt(II) complex
D=the concentration of Pt(II) complex after reacted with hydroxyapatite FIGS. 1 and 2 depict the adsorption percentages to hydroxyapatite calculated from $^{31}P$ NMR, $^1H$ NMR, and AAS. These results showed that cis-Pt($NH_3$)$_2$(MDP) and Pt(dach)(MDP) adsorb to hydroxyapatite as Pt(II) complexes. Pt(dach)(MDP) adsorbed slightly more than cis-Pt($NH_3$)$_2$(MDP), and both Pt(dach)(MDP) and cis-Pt($NH_3$)$_2$(MDP) adsorbed quite significantly more than carboplatin. When Pt(II) complexes were reacted with 100 mg of hydroxyapatite, the adsorption percentages of cis-Pt($NH_3$)$_2$(MDP) was 69.3%, and that of Pt(dach)(MDP) was 79.6%.

EXAMPLE 15

In Vivo Tumor Assay

Male NCr-nude mice, 6-8 weeks of age, were fed ad libitum water (reverse osmosis, 0.17% Cl) and an autoclaved standard rodent (NIH31) diet consisting of: 18% protein; 5% fat; 5% fiber; 8% ash; and 3% minerals. Mice were housed in microisolators on a 12-hour light cycle at 22° C. (72° F.) and 40%-60% humidity. Mice were implanted subcutaneously with $5\times 10^6$ DU145 human prostate cancer cells in the flank. Tumors were monitored initially twice weekly, and then daily as the neoplasms reached the desired size, approximately 100 $mm^3$ (100 mg). When the DU145 prostate carcinomas attained this size, the animals were pair-matched into the various treatment groups. Estimated tumor weight was calculated using the formula: Tumor Weight (mg)=$(w^2\times L)/2$, where w=width and l=length in mm of the tumor.

Representative compounds of the instant invention were injected intraperitoneally to the animals and found to possess significant antitumor activity. See FIGS. 3-6, below.

The compounds of the instant invention generally can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts can be formed by taking about 1 equivalent of a compound of the invention, (e.g., Compound C, below), and contacting it with about 1 equivalent or more of the appropriate corresponding acid of the salt which is desired. Work-up and isolation of the resulting salt is well-known to those of ordinary skill in the art.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration. Accordingly, the present invention includes within its scope pharmaceutical compositions comprising, as an active ingredient, at least one compound of the invention in association with a pharmaceutically acceptable carrier.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

In general, an effective dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

A preferred dosage range is 0.01 to 10.0 mg/kg of body weight daily, which can be administered as a single dose or divided into multiple doses.

While various embodiments of the present invention have been described in detail, it is apparent that further modifications and adaptations of the invention will occur to those skilled in the art. However, it is to be expressly understood that such modifications and adaptations are within the spirit and scope of the present invention. All of the references cited herein are hereby incorporated by reference in their entirety.

What is claimed is:

1. A complex according to formula III:

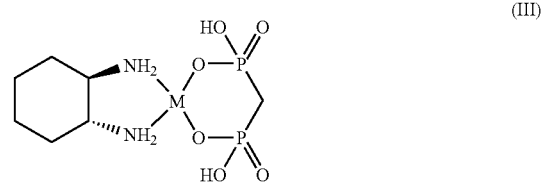

wherein M is Pt(II) or Pd(II);
or a pharmaceutically acceptable salt thereof.

2. A complex according to formula IV:

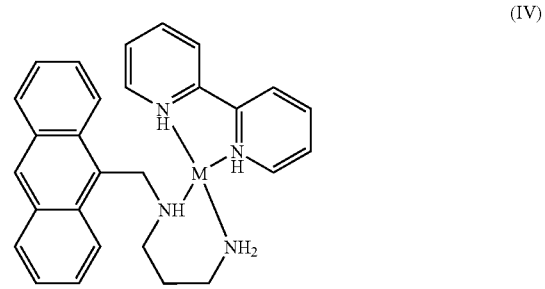

wherein M is Pt(II) or Pd(II);
or a pharmaceutically acceptable salt thereof.

3. A complex according to formula V:

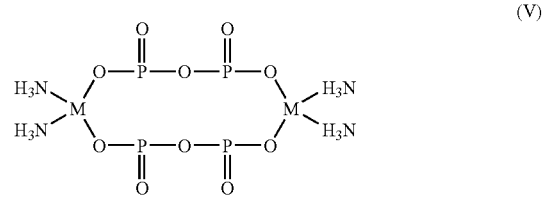

wherein M is Pt(II) or Pd(II);
or a pharmaceutically acceptable salt thereof.

4. A complex according to formula VI:

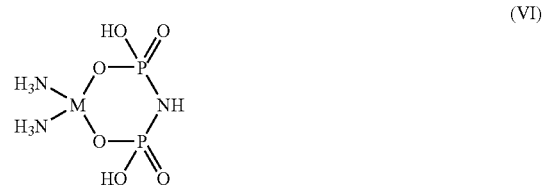

wherein M is Pt(II) or Pd(II);
or a pharmaceutically acceptable salt thereof.

5. A complex according to formula VII:

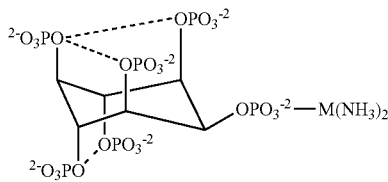

(VII)

wherein M is Pt(II) or Pd(II);
or a pharmaceutically acceptable salt thereof.

6. A complex according to formula VIII:

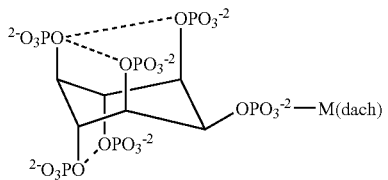

(VIII)

wherein M is Pt(II) or Pd(II);
or a pharmaceutically acceptable salt thereof.

7. A complex according to any one of claims 1,2,3,4, 5, or 6, wherein M is Pt(II), or a pharmaceutically acceptable salt thereof.

8. A method of delivering a therapeutically effective amount of a cytostatic or cytotoxic agent to a subject in need thereof, said method comprising administering a therapeutically effective amount of a compound according to any one of claims 1, 2, 3, 4, 5, or 6, or a pharmaceutically acceptable salt thereof, to said subject in need thereof.

9. The method according to claim 8, wherein said cytostatic or cytotoxic agent is delivered at or to bone tissue within said subject.

10. The method according to claim 9, wherein said cytostatic or cytotoxic agent is delivered at or to bone tissue within said subject on which or in which cancer cells are present.

11. The method according to claim 10, wherein said therapeutically effective amount of said cytostatic or cytotoxic agent is an amount effective to treat said cancer cells.

12. A method according to claim 8, wherein said cytostatic or cytotoxic agent is platinum.

13. A method according to claims 8, wherein said cytostatic or cytotoxic agent is palladium.

14. A method of delivering a therapeutically effective amount of a cytostatic or cytotoxic agent to a subject in need thereof, said method comprising administering a therapeutically effective amount of a compound according to claim 3, or a pharmaceutically acceptable salt thereof, to said subject in need thereof.

15. The method according to claim 14, wherein said cytostatic or cytotoxic agent is delivered at or to bone tissue within said subject.

16. The method according to claim 15, wherein said cytostatic or cytotoxic agent is delivered at or to bone tissue within said subject on which or in which cancer cells are present.

17. The method according to claim 16, wherein said therapeutically effective amount of said cytostatic or cytotoxic agent is an amount effective to treat said cancer cells.

18. A method according to any one of claims 14, 15, 16, or 17, wherein said cytostatic or cytotoxic agent is platinum.

19. A method according to any one of claims 14, 15, 16, or 17, wherein said cytostatic or cytotoxic agent is palladium.

20. A method according to claim 8, wherein said therapeutically effective amount of said cytostatic or cytotoxic agent is an amount effective to reduce skeletal complications.

21. A method according to claim 8, wherein said therapeutically effective amount of said cytostatic or cytotoxic agent is an amount effective to treat myeloma bone disease, metastases of breast cancer, metastases of prostate cancer.

22. A complex according to claim 5, wherein M is platinum.

23. A complex according to claim 5, wherein M is palladium.

* * * * *